United States Patent [19]

Byrne et al.

[11] Patent Number: 4,957,490

[45] Date of Patent: Sep. 18, 1990

[54] INJECTION DEVICE

[75] Inventors: Phillip O. Byrne; Penelope R. Sisson; Harry R. Ingham, all of Newcastle-upon-Tyne, England

[73] Assignee: National Research Development Corporation, London, England

[21] Appl. No.: 131,228

[22] Filed: Dec. 10, 1987

[30] Foreign Application Priority Data

Dec. 16, 1986 [GB] United Kingdom ............... 8630016

[51] Int. Cl.⁵ ............................................. A61M 5/00
[52] U.S. Cl. .................................... 604/197; 604/110; 604/194
[58] Field of Search .......................... 604/192–197, 604/110

[56] References Cited

U.S. PATENT DOCUMENTS

| | | | |
|---|---|---|---|
| 3,890,971 | 6/1975 | Leeson et al. | 604/197 |
| 4,148,316 | 4/1979 | Xanthopoulos | 604/192 |
| 4,664,653 | 5/1987 | Sagstetter et al. | 604/197 |
| 4,834,717 | 5/1989 | Haber et al. | 604/193 |

Primary Examiner—John D. Yasko
Assistant Examiner—Adam J. Cermak
Attorney, Agent, or Firm—Cushman, Darby & Cushman

[57] ABSTRACT

An injection device which is devised to be safer in use than many prior such devices comprises a generally cylindrical barrel section which is substantially closed at its first end but has an aperture in that end to allow an injection needle to pass through it, a needle support member to slide within the barrel section and shaped to receive one end of a liquid container such as an ampoule of anaesthetic, and a plunger mounted at the other end of the barrel section for axial movement in said section. The plunger is adapted both to express liquid from the liquid container when the plunger is advanced within the barrel and also to interconnect with either the needle support member or the liquid container, whereby withdrawal of the plunger withdraws both the liquid container and also the needle and its support member into the barrel section for disposal.

13 Claims, 5 Drawing Sheets

INJECTION DEVICE

The present invention is an injection device which has been devised to be of enanced safety in use compared with many prior such devices. It is of particular value as applied to the application of dental injections but is potentially of merit for other injection purposes.

Dentists generally nowadays apply local anaesthetic to the area of the gums using a gun type of anaesthetic injector. Injectors of this type comprise a steel cylinder and a hand-tolerated plunger working within the cylinder. Anaesthetic is introduced in the form of a glass ampoule into the cylinder and injection is via a fine-bore, double-ended needle. The operating procedure requires the dentist to fit the needle to the body of the gun before or after inserting the ampoule of anaesthetic into the cylinder and thereby to cause the ampoule to be penetrated by the inner end of the needle. After removal of a protective sheath from the outer end of the needle, the anaesthetic may be injected as required.

While such devices have proved to be very useful, the removal and disposal of the needle after use is a potentially hazardous operation in that it entails the handling of a double-ended needle, of which at least the outer end (and often also the inner end) is contaminated by the patient's body fluids, for example blood or saliva, which may contain infectious agents. Thus there is a serious risk of the dentist accidentally piercing his own skin and thereby introducing an infection or other contaminant into his body. An attempt to re-sheath the outer end of the needle before removing it from the cylinder of the injection gun entails its own dangers and still leaves the inner end of the needle exposed. The removal of the needle and the ampoule from the cylinder before again using the injection gun, and the subsequent disposal of needle and ampoule, pose a serious potential hazard to the dentist, his staff and members of the general public.

The present invention has been devised with the object of reducing or eliminating these hazards which characterise use of existing such devices, and in Particular of eliminating the need to handle the double-ended needles after use.

The injection device according to the present invention comprises a generally cylindrical barrel section, substantially closed at a first end thereof but having an aperture in said closed end to permit passage of an injection needle therethrough, a needle support member carrying an injection needle and of such dimensions as to fit within the barrel section for sliding movement axially therein between a forward position in which said needle extends through said aperture and a rearward position in which said needle lies wholly within said barrel section, said needle support member further being, shaped to receive one end of a liquid container also within said barrel section, and a plunger, mounted at the second end of said barrel section for axial movement therein and adapted by forward said movement to express liquid from a said container and to interconnect with either the needle support member or a said liquid container such that subsequent rearward movement of said plunger withdraws the needle support member into its rearward position.

In use of the injection device according to the invention, the needle support member, carrying a conventional double-ended needle, is located within the barrel section with one end of the needle projecting through the aperture at the first end of the barrel section. At presentation, the projecting end of the needle will be protected by an enclosing, disposable plastic sheath. A conventional liquid ampoule is introduced into the barrel section and when the plunger is depressed it presses the ampoule into contact with the support member, where the ampoule is pierced by the inner end of the needle. Further operation of the plunger expels liquid from the ampoule through the needle for injection in the usual way. However, when the injection is completed, withdrawal of the plunger also achieves withdrawal of the ampoule and of the needle support member into the barrel section until the outer end of the needle is no longer exposed. The barrel section, ampoule and needle nay then together be disconnected from the plunger and discarded with the needle fully protected, without any risk of accidental injury to the user.

The generally cylindrical barrel section may be made of steel as is usual but, since the intention is that it should be discarded after a single use, it is preferred that it be made of a synthetic plastics material. The barrel section may be similar to that of a conventional dental injection gun but is preferably a little longer, to permit full retraction of the needle with the ampoule into the barrel.

The needle support member may conveniently take the form of a short, generally cylindrical plug or bung, of slightly smaller radial diameter than the internal diameter of the barrel section and having the needle extending axially through it. The needle support is shaped to receive one end of a liquid container within the barrel section and may either merely be internally somewhat tapered so as to locate the container centrally within the barrel section and assist its alignment with the inner end of the needle, or may positively engage and grip the container. For example, the needle support member may incorporate connector means designed to be a snap fit over the outside of the neck of a conventional ampoule. Thus in one form the needle support member may be a unitary moulding in a resilient synthetic plastics material, having an inturned short cylindrical extension or collar to snap over the ampoule neck. In a preferred form described below, the needle support member is designed to permit the plunger to pass into the container in a forward direction and to remain interconnected to the needle support member when the plunger is being withdrawn.

The plunger is mounted at the second end of the barrel section for axial movement within that section. The plunger may be mounted in a cap designed to fit over or within the open barrel end and having an axial aperture to support and guide the plunger. The cap and plunger may themselves be intended to be discarded with the barrel, ampoule and needle after a single use, in which case the cap may be hinged to the barrel as in a conventional dental injection gun, to permit insertion of the ampoule. However in the interest of keeping costs down to acceptable levels, it is strongly preferred for the cap and barrel to be mutually separable before and after use, so that the cap and plunger may be used several or many times before eventually being replaced. To that end, the cap may be a simple tight push-fit into or on to the end of the barrel, or the connection may be a screw connection of a spring-loaded, self-locking type, for example a bayonet-type connection.

Ampoules of anaesthetic for dental injection guns are usually manufactured to a standard format, having a bung slidable within the ampoule and urged down the internal length of the ampoule by a plunger. To enable such conventional ampoules to be used with the improved gun of the present invention, the plunger may similarly be of such dimensions, at its free end, as to enter a conventional ampoule and push the bung. A second function to be performed by the plunger is to interconnect with either the needle support member or, if the latter is of the type which locks on to the liquid container, the container itself, so that withdrawal of the plunger also retracts the liquid container and the needle.

In a preferred form of the invention, the interconnection is between the needle support member and the plunger. The means for achieving this interconnection may very conveniently take the form of one or more resilient elongated extensions of the needle support member, adapted to extend beyond the length of the liquid container and to engage in one or more projections expanding laterally from the plunger. Preferably the extensions positively engage the projections only in the direction of withdrawal of the plunger. Advantageously, provision is made for disengagement of the projections after withdrawal of the plunger, to simplify subsequent disposal of the ampoule, needle support member and cylinder.

In an alternative, less preferred form of the invention, the plunger is designed to h=able to engage the ampoule itself. A very convenient way of achieving this is for the plunger to carry, at or adjacent to its end which enters the ampoule, a radially expandable plug. For example, the plug may be an O-ring of rubber or resilient synthetic plastics material, which by axial pressure may be caused to expand radially to engage the inner surface of the ampoule. The radial expansion of the plunger plug may be achieved by forming the plunger in two coaxial sections, which by relative axial movement are able to apply axial pressure on the plug as desired.

As a preferred feature of the injection device according to the present invention, locking means may be provided to retain the ampoule and needle in the retracted position within the barrel section after use. A simple preferred mechanical form of the locking means is a radial projection from the needle support member and a corresponding detent in the inner face of the barrel section at a point corresponding to the retracted position of the needle support member. As an alternative, the needle support member and barrel section may be locked together chemically after use, by providing their abutting surfaces with suitable chemically interacting coatings.

Figure 1:
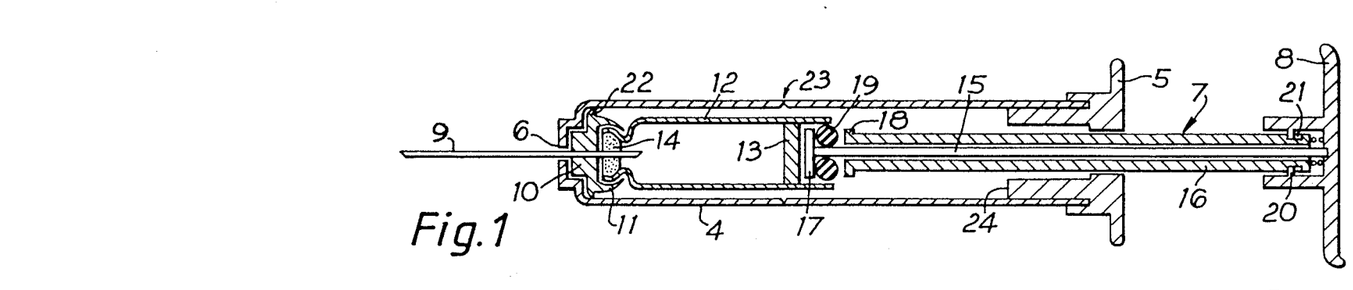
FIG. 1 is a longitudinal sectional view of the first embodiment of the device, in a condition wherein it is ready for use.
Figure 2:
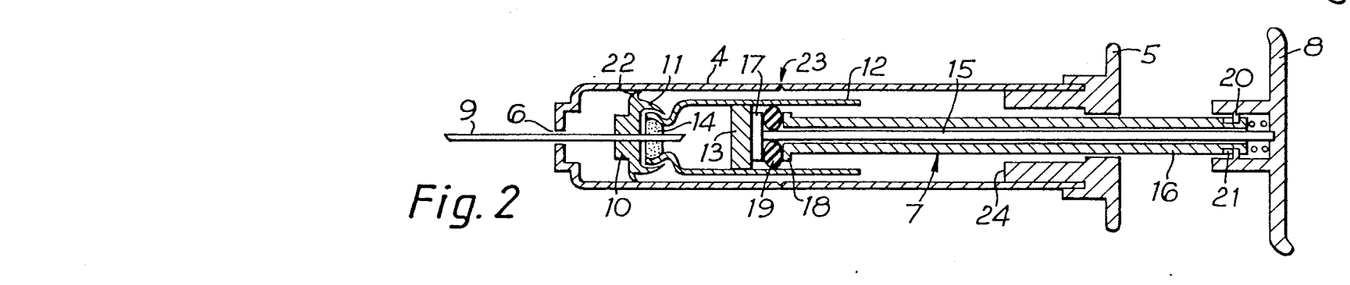
FIG. 2 is a view corresponding to FIG. 1, shortly after the device has been used to give an injection and with the needle and ampoule partly retracted.
Figure 3:
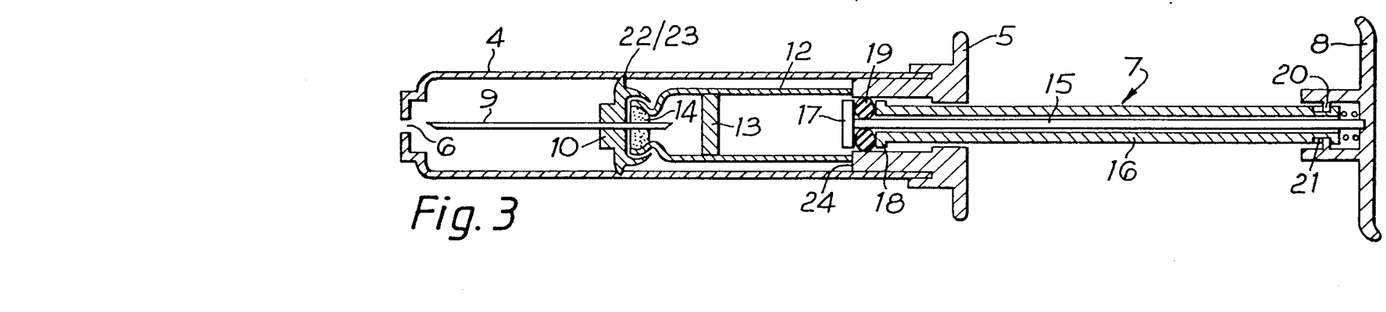
FIG. 3 is a view corresponding to FIGS. 1 and 2, with the needle and ampoule fully retracted, shortly before they are discarded.
Figure 4:
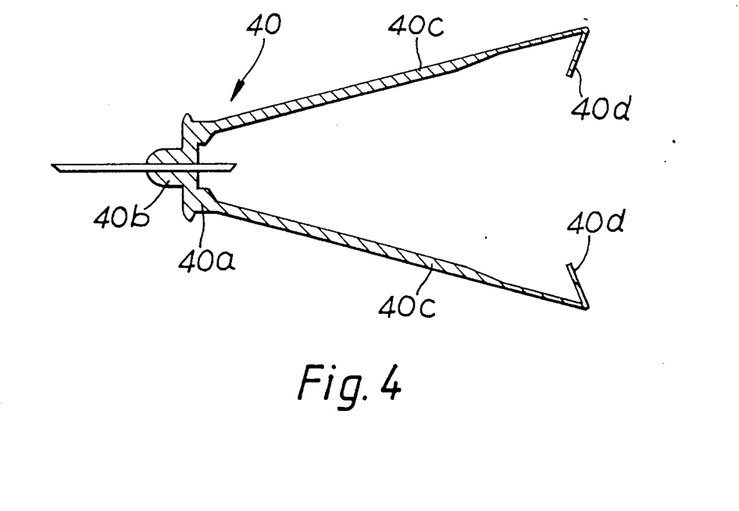
FIG. 4 is a longitudinal sectional view of the needle support member which is a component of the second embodiment of the device.
Figure 5:
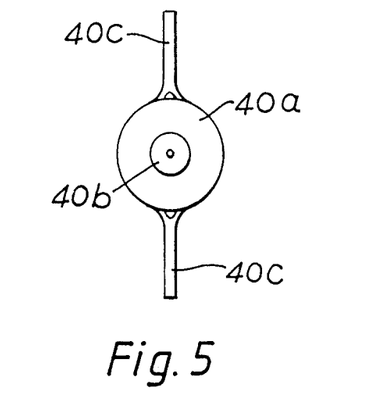
FIG. 5 is an elevation from the front of the support member of FIG. 4.

The invention will now be further described with reference to the accompanying drawings, wherein three specific embodiments of the invention are illustrated. The first embodiment, illustrated in FIGS. 1 to 3, is of the type wherein the plunger engages the ampoule itself. In the second and third embodiments, which are illustrated in FIGS. 4 to 11 and which represent particularly preferred forms of the invention, the plunger is designed to engage the needle support member.

Referring firstly to FIGS. 1 to 3, the dental injection device illustrated therein comprises a barrel section 4, closed at one end by a cap 5 and having a small aperture 6 at its other end through which the needle for injection is able to project. Extending axially through the cap 5 into the interior of the barrel 4 is a plunger 7, which may be moved linearly by means of a handle 8 on its outer end.

A fine-bore, double-ended needle 9 is carried by a needle support in the form of a short, generally cylindrical plug 10, which is free to slid=axially within the barrel 4. The face of the plug 10 remote from the aperture 6 is shaped to form an inturned cylindrical extension 11, which is of such dimensions as to clip resiliently over the neck of a conventional ampoule 12 of anaesthetic, introduced into the barrel 4 by the dentist. The ampoule 12 is sealed by a plug 13, which is able to slide within the ampoule to eject liquid. When the ampoule is first introduced into the barrel 4, the inner end of the needle 9 pierces a cap 14 which covers the top of the ampoule 12.

The plunger 7 is constructed of two coaxial parts, which may conveniently be called an inner plunger 15 and outer plunger 16. The inner plunger 15 terminates in a flat disc-shaped head 17 which is able to enter the wider end of the ampoule 12 to push the plug 13. Thus, beginning with the injection device in the position illustrated in FIG. 1, the plunger is first depressed slightly, following the normal practice, to ensure free flow of anaesthetic through the needle. After the needle 9 has been introduced into the patient's gum, movement of the plunger further into the barrel 4 by means of the handle 8, which is secured to the inner plunger 15, causes anaesthetic from the ampoule 12 to be ejected via the needle 9.

The outer plunger 16 terminates in an annular head 18 and a resilient O-ring 19 is located between the head 17 of the inner plunger 15 and the head 18 of the outer plunger. Thus relative axial movement of the plungers 15 and 16 may squeeze the O-ring 19 so as to cause it to expand radially into contact with the inner face of the ampoule 12 as shown in FIG. 2.

A spring located in the handle 8 normally urges the plunger heads 17 and 18 towards each other and thereby squeezes the O-ring 19 into gripping engagement with the ampoule. Relative axial movement of the plungers 15 and 16 is limited by lateral pins 20 on the handle 8 extending into a pair of "windows" 21 in the outer plunger 16. When the handle 8 is pressed in order to advance the plunger assembly into the barrel 4, the pressure on the O-ring is released and the plunger can push the plug 13 into the ampoule.

When the injection is completed, the pull on the handle 8 necessary to withdraw the plunger assembly also causes the heads 17 and 18 to approach each other and cause the O-ring 19 to engage the inner face of the ampoule 12. Thus the ampoule 12 and the needle support member 10 are retracted with the plunger until the needle lies wholly within the barrel 4.

At this stage, the end of the ampoule 12 abuts a cylindrical inward extension 24 of the cap 5. Simultaneously a circumferential projection 22 on the plug 10 locks into an indent 23 on the inner face of the barrel 4 and retains the plug 10 and ampoule 12 against further movement relative to the barrel. Further retraction of the plunger causes the O-ring 19 to slide against friction until it disengages itself from the ampoule 12, which is left in its locked position within the barrel 4.

The barrel may now be separated from cap 5 (for example by a twisting "bayonet" action) and the barrel and its contents, namely the needle and ampoule, may be discarded safely without handling of these potentially dangerous contents.

Figure 6:
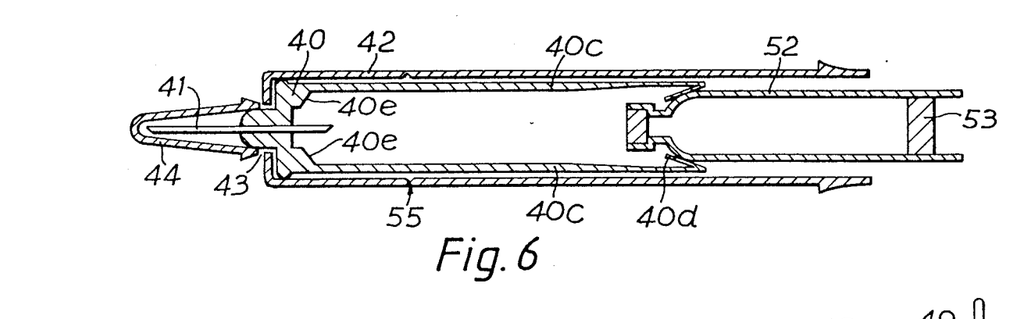
FIG. 6 is a longitudinal sectional view of the cylindrical barrel section of the second embodiment, with the needle support member in place and the ampoule ready for insertion.

Turning now to FIGS. 4 to 9 of the accompanying drawings, the second embodiment of the injection device according to the present invention makes use of a different form of needle support device in the form of a "needle carriage" 40. The carriage 40 (FIGS. 4 and 5) has a short cylindrical body part 40a, a forwardly-projecting boss 40b and, in the illustrated form, two rearwardly-extending arms 40c, each terminating in an in-turned claw 40d. As shown in FIG. 6, the carriage 40, with a needle 41 extending axially through the body part 40a and boss 40b, is a snug sliding fit within a cylindrical barrel 42 and, when fully inserted in the barrel, allows the boss and needle to project through an aperture 43 in the otherwise closed end of the barrel. The projecting end of the needle is at this stage protected by a sheath 44.

Figure 7:
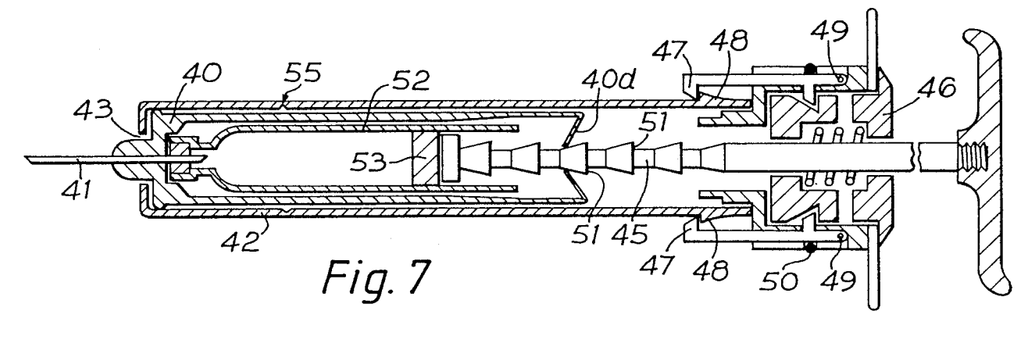
FIG. 7 is a longitudinal sectional view of the complete dental injection device in its second embodiment, just before an injection is administered.

When an ampoule 52 of anaesthetic is introduced into the open end of the barrel 42, it can readily deflect the resilient claws 40d and be further inserted as far as the point where it encounters the inner end of the needle 41, on to which it is guided by inclined internal shoulders 40e on the carriage 40. The ampoule is shown in FIG. 7 in its position of use. At this point, the claws 40d have resumed their natural at-rest position.

A single plunger 45 is supported axially within the barrel 42 by means of a cap 46 which locks on to the open end of the barrel. The cap is held in place by means of claws 47, which engage an annular shoulder 48 on the barrel 42. The claws 47 are pivoted at 49 and are normally urged into the position shown in FIGS. 7 and 8 by a circular sPring 50. By virtue of the claws 47, the cap 46 and barrel 42 are locked together against inadvertent separation until, by a mechanism described below, the lock is released by complete retraction of the plunger, ampoule and needle.

The plunger 45 has a series of indentations 51 along a part of its length and these can easily deflect the claws 40d as the plunger advances. Thus forward movement of the plunger pushes a plug 53 in the ampoule 52 and expels anaesthetic through the needle 41 for injection in the manner of a conventional dental gun.

When injection is complete, the plunger 45 is withdrawn and the claws 40d are now captured by the indentations 51, with the result that the carriage 40 and the ampoule 52 are withdrawn with the plunger, the needle being retracted into the barrel. When retraction is complete (FIG. 8), the claws 40d are engaged and deflected by a cylindrical projection 54 on the cap 46, enabling the indentations 51 to pass those claws so that further withdrawal of the plunger 45 leaves the needle carriage, needle and ampoule within the barrel. At this point, a peripheral projection 40f on the needle carriage locks into an indent 55 on the inner face of the barrel and secures the carriage and associated components within the barrel.

Further withdrawal of the plunger 45 moves a spring-loaded piston 56 within the cap 46 in such a direction (see FIG. 9) that an inclined face 57 of the piston deflects the claws 47 against the pressure of the circular spring 50 and disengages them from the annular shoulder 48. Thus the barrel and its contents may now be separated from the cap-and-plunger assembly and safely discarded.

It will be observed that those items which have been used in the injection procedure and thereby exposed to the risk of contamination have thus been separated and discarded without any handling by the user of the dental injection gun.

The third embodiment of the injection device according to the invention, which will now be described, resembles the second embodiment illustrated in FIGS. 4 to 9 except in those details illustrated in FIGS. 10 and 11. As illustrated, in this third embodiment, the device for interconnecting and subsequently disconnecting the plunger and the needle carriage takes a different form.

Figure 10:
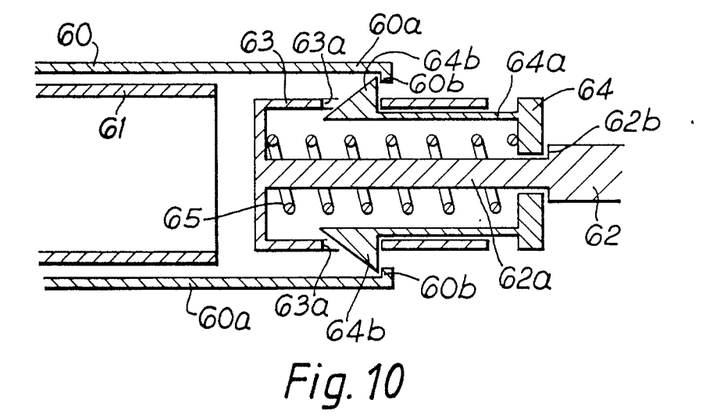
FIG. 10 is a longitudinal sectional view of a detail of a third embodiment of the invention, showing the means for interconnecting the plunger and the needle support member in the interconnecting condition.
Figure 11:
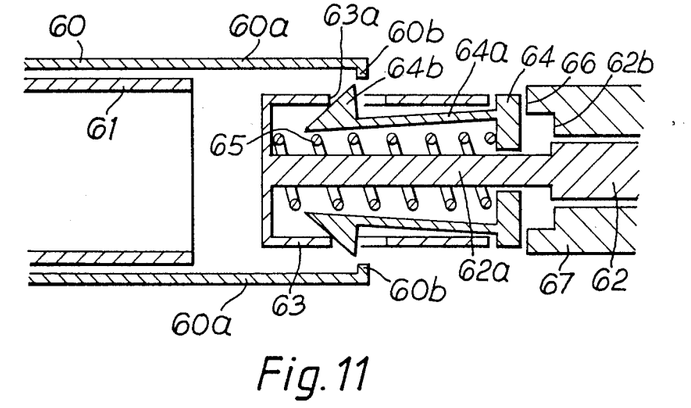
FIG. 11 is a view corresponding to FIG. 10, showing the plunger and needle support member disconnected from each other.

Referring to FIGS. 10 and 11, the needle carrier 60 has two or more rearwardly-extending arms 60a, each having an inturned lip 60b. As illustrated, the arms 60a extend beyond the end of an ampoule 61 located within the needle carrier such that the lips 60b may be captured by the plunger. The plunger 62 has a forward extension 62a of reduced diameter so as to form a shoulder 62b and the extension 62a carries a generally cylindrical cover 63, of such radial dimension as to be able to slide within the ampoule 61 and advance the conventional plug therein (not shown) in order to express anaesthetic from the ampoule in the usual manner.

Slideably mounted upon the extension 62a of the plunger 62 within the cover 63 is a bush 64 having resilient arms 64a terminating in barbs 64b. A helical compression spring 65 urges the bush 64 against the shoulder 62b and, when the bush 64 is in its most rearward position, the barbs 64b project radially outwardly through windows 63a in the cover 63 and are thereby able to engage the lips 60b.

When the plunger 62 is first advanced within the syringe barrel (not shown), the barbs 64b are readily deflected by the edge of the lips 60b and by the edge of the ampoule 61, thus allowing the plunger to enter the ampoule and express anaesthetic through the syringe needle. However, when injection is completed and the plunger is subsequently withdrawn from the ampoule, the barbs 64b spring radially outwardly to engage the lips 60b, such that the needle carrier is withdrawn with the plunger until the needle lies wholly within the syringe barrel.

Figure 8:
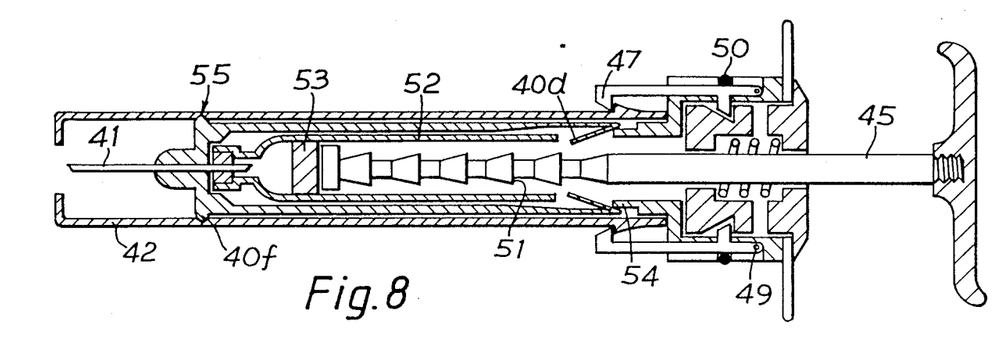
FIG. 8 is a view corresponding to FIG. 7, with the ampoule and needle support member fully withdrawn.
Figure 9:
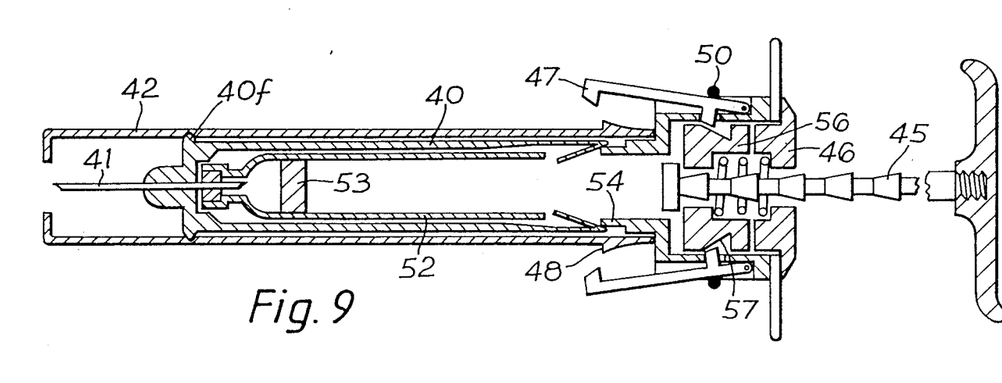
FIG. 9 is a view corresponding to FIGS. 7 and 8, with the barrel, ampoule and needle support member disconnected from the plunger assembly before they are discarded.

On further withdrawal of the plunger, the bush 64 abuts an annular end-stop 66 projecting from the cap 67 of the syringe. The plunger 62 and cover 63 are able to continue to move axially by a short distance relative to the bush 64, against the resistance of spring 65, and this short relative movement of cover 63 and bush 64 causes the barbs 64b to ride radially inwardly over the forward edges of the windows 63a; in this way, the barbs clear the lips 60b and the plunger becomes disconnected from the needle carrier 60. Simultaneously, claws on the cap 67 similar to the claws 47 of FIGS. 7 to 9 are deflected to enable the cap to be separated from the syringe barrel. The barrel and its contents may now be discarded as before.

We claim:

1. An injection device comprising a generally cylindrical barrel section, substantially closed at a first end thereof but having an aperture in said closed end to permit passage of an injection needle therethrough, a needle support member, an injection needle carried by said support member, said support member being dimensioned to fit within said barrel section and to move axially therein between a forward position in which said needle extends through said aperture and a rearward position in which said needle lies wholly within said barrel section, said needle support member further being shaped to receive one end of a liquid container also lying within said barrel section, a plunger, mounted at the second end of said barrel section for axial movement into and out of said liquid container, and connector means adapted to connect upon initiation of said plunger axial movement into said liquid container, said plunger to one of said liquid container and said support member, said plunger having a leading end portion, and a trailing end portion, said leading end portion being closer to said first end of said syringe barrel than said trailing end portion, said liquid container and said support member each having a leading end portion and a trailing end portion, said leading end portions of said liquid container and said support member being closer to said first end of said syringe barrel than said trailing end portion, said connector means having mutually connecting first and second members, the first member being located adjacent the leading end portion of said plunger relative to initial movement thereof into said liquid container and the second member being located at the trailing end portion of said one of said liquid container and said support member relative to said initial movement, whereby subsequent axial movement of said plunger in a direction away from said closed end of said barrel section moves said needle to said rearward position.

2. An injection device according to claim 1, wherein said needle support member is a short, generally cylindrical plug, of slightly smaller radial diameter than the internal diameter of said barrel section, and said injection needle extends axially through said plug.

3. An injection device according to claim 2, wherein said needle support member includes engagement means to attach said needle support member to a said liquid container.

4. An injection device according to claim 3, wherein said connector means comprises a plug carried upon the end of said lunger which enters said liquid container, and means to extend said plug radially into contact with said liquid container.

5. An injection device according to claim 4, wherein said plunger is formed in two coaxial sections and said radial expansion of said plug is effected by relative axial movement of said two coaxial sections.

6. An injection device according to claim 2, wherein said connector means comprises at least one elongated extension from said plug, said at least one extension being adapted to extend beyond said liquid container and to resiliently engage at least one lateral projection from said plunger.

7. An injection device comprising
   (a) a generally cylindrical barrel section,
   (b) said barrel section being substantially closed at a first end thereof but having an aperture in said closed end to permit passage of an injection needle therethrough,
   (c) a hollow needle for injection liquid into human tissue,
   (d) a needle support member in the form of a short generally cylindrical plug of lesser diameter than the internal diameter of said barrel section and having said hollow needle extending axially through said plug,
   (e) said plug and needle together being movable axially within said barrel section between a forward position in which said needle extends through said aperture and a rearward position in which said needle lies wholly within said barrel section,
   (f) a liquid container lying within said barrel section in engagement with said needle support member,
   (g) a plunger mounted at a second end of said barrel section for axial movement in said barrel section into and out of said liquid container, said plunger having a forward end and a formation at said forward end, and
   (h) at least one elongated extension from said plug, adapted to connect said plug to said formation of said plunger upon initiation of axial movement of said plunger into said liquid container, whereby said needle and plug may together be withdrawn by said plunger into said rearward position of said needle.

8. An injection device according to claim 7, wherein said plunger is mounted in a cap for removable attachment to said barrel section.

9. An injection device according to claim 8, wherein said at least one elongated extension from said plug is adapted to resiliently engage in at least one lateral projection from said plunger.

10. An injection device according to claim 9, having means to disengage said at least one elongated extension from said at least one lateral projection when said plunger is withdrawn.

11. An injection device according to claim 10, comprising a series of projections separated from each other by indentations.

12. An injection device according to claim 10, wherein said at least one lateral projection from said plunger comprises at least one resiliently-supported barb.

13. An injection device according to claim 10, having locking means to retain said liquid container and said needle in said rearward position within said barrel section after use of said device.

* * * * *

UNITED STATES PATENT AND TRADEMARK OFFICE
CERTIFICATE OF CORRECTION

PATENT NO. : 4,957,490

DATED : September 18, 1990

INVENTOR(S) : BYRNE et al.

It is certified that error appears in the above-identified patent and that said Letters Patent is hereby corrected as shown below:

Column 1, line 5, change "ehanced" to --enhanced--.

Column 1, line 12, change "hand-tolerated" to --hand-operated--.

Column 1, line 42, change "Particu-" to --particu--.

Column 1, line 56, delete "," after "ing".

Column 3, line 28, change "h=able" to --be able--.

Column 4, line 39, change "slid=axially" to --slide axially--.

Column 5, line 64, change "sPring" to --spring--.

Column 7, line 67 change "lunger" to --plunger--.

UNITED STATES PATENT AND TRADEMARK OFFICE
CERTIFICATE OF CORRECTION

PATENT NO. : 4,957,490

DATED : September 18, 1990

INVENTOR(S) : BYRNE et al.

It is certified that error appears in the above-identified patent and that said Letters Patent is hereby corrected as shown below:

Column 8, line 19, change "injection" to --injecting--.

Signed and Sealed this

Seventh Day of April, 1992

Attest:

HARRY F. MANBECK, JR.

*Attesting Officer*    *Commissioner of Patents and Trademarks*